United States Patent
Geistlich et al.

[11] Patent Number: 5,837,278
[45] Date of Patent: Nov. 17, 1998

[54] RESORBABLE COLLAGEN MEMBRANE FOR USE IN GUIDED TISSUE REGENERATION

[75] Inventors: Peter Geistlich, Stansstad, Switzerland; Zdenek Eckmayer, Weinheim, Germany; Philip Boyne, Loma Linda, Calif.

[73] Assignee: Ed Geistlich Söhne AG Für Chemische Industrie, Switzerland

[21] Appl. No.: 669,448
[22] PCT Filed: Jan. 4, 1995
[86] PCT No.: PCT/GB95/00008
§ 371 Date: Nov. 18, 1996
§ 102(e) Date: Nov. 18, 1996
[87] PCT Pub. No.: WO95/18638
PCT Pub. Date: Jul. 13, 1995

[30] Foreign Application Priority Data

Jan. 6, 1994 [GB] United Kingdom .................. 9400163

[51] Int. Cl.$^6$ ............................ A01N 25/34; A61L 15/16
[52] U.S. Cl. ........................... 424/444; 424/443; 424/402
[58] Field of Search ................................. 424/443, 444, 424/402

[56] References Cited

U.S. PATENT DOCUMENTS

| | | | |
|---|---|---|---|
| 4,060,081 | 11/1977 | Yannas et al. | 128/156 |
| 4,185,011 | 1/1980 | Eckmayer et al. | 260/123.7 |
| 4,674,488 | 6/1987 | Nashef et al. | 128/92 |
| 4,725,671 | 2/1988 | Chu et al. | 514/21 |
| 5,028,695 | 7/1991 | Eckmayer et al. | 530/356 |
| 5,573,771 | 11/1996 | Geistlich et al. | 424/422 |

FOREIGN PATENT DOCUMENTS

| | | |
|---|---|---|
| 0044624 | 10/1984 | European Pat. Off. . |
| 0331786 | 9/1989 | European Pat. Off. . |
| 2631909 | 2/1977 | Germany . |
| 3203957 | 8/1983 | Germany . |
| 3607075 | 9/1986 | Germany . |
| 1518748 | 7/1978 | United Kingdom . |
| 1525792 | 9/1978 | United Kingdom . |
| 2174909 | 11/1986 | United Kingdom . |
| 88 08305 | 11/1988 | WIPO . |
| 90 13302 | 11/1990 | WIPO . |
| 93 02718 | 2/1993 | WIPO . |
| 93 10722 | 6/1993 | WIPO . |

*Primary Examiner*—Thurman K. Page
*Assistant Examiner*—Kathryne E. Shelborne
*Attorney, Agent, or Firm*—Rothwell, Figg, Ernst & Kurz, p.c.

[57] ABSTRACT

The invention is concerned with wound healing and in particular with the use of a collagen-containing membrane in guided tissue regeneration. The invention provides a resorbable collagen membrane for use in guided tissue regeneration wherein one face of the membrane is fibrous thereby allowing cell growth thereon and the opposite face of the membrane is smooth, thereby inhibiting cell adhesion thereon.

24 Claims, 1 Drawing Sheet

RESORBABLE COLLAGEN MEMBRANE FOR USE IN GUIDED TISSUE REGENERATION

The present invention is concerned with wound healing and in particular with the use of a collagen-containing membrane in guided tissue regeneration.

In any situation, such as following surgery especially oral or dental surgery, where wound healing is desirable, it has proved to be difficult to provide conditions which prevent ingrowth of other tissues into the area where regeneration is required. Thus, for example, where a substantial portion of a tooth root is removed due to decay or disease, it is desirable that healthy bone regeneration occurs to replace the bone tissue removed. However, it has been found that the cavity left by removal of the bone is quickly filled by connective tissue and that this ingrowth of connective tissue effectively prevents bone regeneration.

In order to overcome such difficulties the technique known as "guided tissue regeneration" has been developed. In this method a membrane is surgically inserted around the periphery of the wound cavity. The membrane prevents or hinders the invasion of the wound cavity by unwanted cell types and thus allows the preferred cells to grow into the cavity, thereby healing the wound.

Two membrane types are currently used in guided tissue regeneration:

1) Synthetic, non-resorbable PTFE membranes, such as Goretex (trade mark); and

2) Synthetic resorbable membranes formed from glycolide and lactide copolymers.

However, both of these membrane types suffer from serious disadvantages. The PTFE membrane, although exhibiting suitable characteristics of porosity, strength and flexibility, remains non-resorbable and therefore a second surgical operation is required to remove the membrane. The requirement for further surgical procedures may be traumatic for the patient and may also damage the new tissue regenerated thus extending the treatment period.

The second membrane type is woven from glycolide and lactide copolymer fibres. Whilst this membrane is resorbable the breakdown products are irritant and this irritance may have undesirable effects on the patient.

Both prior art membranes act as filters, allowing liquids to pass freely and forming a barrier to cells. However, the membrane surface is not "cell-friendly", ie. it does not stabilise blood clots or support cell growth. Consequently, neither of the prior art membranes provide optimal conditions for cell growth and wound healing.

We have now found a membrane with ideal characteristics for guided tissue regeneration.

The present invention provides a resorbable collagen membrane for use in guided tissue regeneration wherein one face of said membrane is fibrous thereby allowing cell growth thereon and the opposite face of said membrane is smooth, thereby inhibiting cell adhesion thereon.

The two opposing sides or faces of the membrane thus have different textures which affect cell growth in different ways.

The smooth side acts as a barrier or filter to hinder cell ingrowth and will prevent undesirable cell types from colonising the cavity described by the membrane through physical separation. By contrast, the fibrous side of the membrane is haemostatic (stabilises blood clots) and aids cell growth by providing a suitable support for the new cells. In use, therefore, the membrane should be inserted with the smooth side outermost and the fibrous side facing the cells where regeneration is desired.

The membrane for use in guided tissue regeneration according to the present invention may be derived from a natural collagen membrane. Being derived from a natural source, the membrane for use in the present invention is totally resorbable in the body and does not form toxic degradation products.

Further the membrane has a tear strength and tear propagation resistance comparable to that of textile material in both wet and dry states. The membrane can therefore be surgically stitched if required. The membrane material is strongly hydrophilic and has good adherence when wet allowing several layers to be stacked together. When moist the material is very elastic which allows irregularly shaped or uneven wounds to be properly covered.

In both humans and animals, certain membranes surrounding important organs and separating different tissues and cells are made up of collagen. Examples of such membranes include the pericardium and placental membranes on the macroscale and basal membranes on the microscale.

Collagen products are now used widely in medicine. A variety of collagen materials are available including soluble collagen, collagen fibres, sponges, membranes and bone implants allowing diverse usage of this material, for example, collagen fibres and sponges for haemostasis, collagen membranes for wound covering or implantation, and injections of soluble collagen in plastic surgery. Nonetheless, it has not previously been recognised that a collagen membrane would be suitable for guided tissue regeneration.

Various artificial collagen-containing membranes have been described in the prior cut and proposed for the dressing or coverage of wounds. Thus, in WO-A-88/08305 (The Regents of The University of California) there is described a composite skin replacement which consists of a layer of human epidermal cells together with a layer of a biosynthetic membrane which may be formed of collagen and mucopolysaccharides. However, the collagen/mucopolysaccharide portion is of uniform texture throughout and does not exhibit the properties of the membrane proposed herein for guided tissue regeneration. Furthermore, such membranes are strongly immunoreactive and can only be used on the donor of the cells. Another artificial collagen-containing membrane is described in DE-A-2631909 (Massachusetts Institute of Technology). This membrane consists of a minimum of two layers, the first layer being a combination of collagen and mucopolysaccharides and the second layer being a synthetic polymer such as a polyacrylate. However, this membrane is totally non-resorbable, the collagenous layer being so tightly cross-linked internally that resorption cannot occur.

The membrane for use in the present invention may be derived directly from naturally occurring membranes which, as far as possible, retain their natural collagen structure. The membrane sources include sections of hide with a grain side, tendons, various animal membranes etc. A preferred source of membrane is the naturally occurring peritoneum membrane, especially taken from calves or piglets. Peritoneum membranes from young pigs aged 6–7 weeks old (weighing 60–80 kg) are especially preferred.

The membrane material for use in the present invention should preferably consist of pure, native (not denatured), insoluble collagen. However, in an animal's body, collagen is accompanied by a number of substances which have undesirable chemical, physical and/or physiological properties. The collagen therefore has to be freed from these substances by purification. Since the nature of such substances varies considerably, enzymatic purification is virtually impossible. It is thus preferable to carry out purification chemically, taking care to minimise any alteration to the chemical structure of the collagen and thus to maintain its original native properties.

According to a further aspect of the present invention we provide a method of preparing a membrane as described above in which a mammalian collagen membrane having a smooth face and a fibrous face is subjected to treatment with alkali to saponify fats and degrade alkali sensitive substances and then acidified to degrade acid sensitive substances, followed by washing, drying, degreasing and optional cross-linking.

During purification, the following changes occur:

non-collagenous proteins are eliminated glycosaminoglycans and proteoglycans are dissolved and eliminated the fats are partially saponified, and totally eliminated.

During such treatment, the following undesirable changes may also occur:

hydrolysis of the amide groups of asparagine and glutamine a shift in the isoelectric point cleavage of crosslinking bonds transamidation, with the formation of isopeptides racemisation of amino acids cleavage of peptide bonds.

The level of amide nitrogen in the membrane serves as an indicator of these changes. For example, it has been found that if the amide nitrogen content falls by about half (ie. from 0.7 mmol/g to 0.35 mmol/g) then more than 95% of the collagen is still present in its native state. The basis of this measurement is the hydrolysis of amide groups in the amino acids asparagine and glutamine:

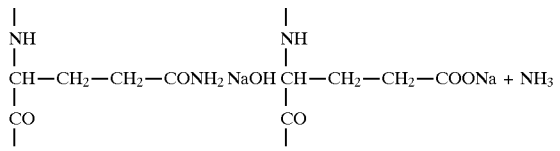

The degree of purification of the collagen can be determined by amino acid analysis. Collagen is hydrolysed to form amino acids, which means that this analysis indicates pure collagen and elimination of non-collagenous proteins but not the denaturing of collagen.

Together with amino acid analysis of the collagen, the glycosamine and proteoglycans content can also be analysed. These contaminants are hydrolysed and the monomeric glycosamine and hexosamine content of the membrane is determined by chromatography. It has been found that the quantity of glycosamine and galactosamine after purification is approximately 1 molecule to 10,000 molecules of amino acids.

In one method of preparing the membranes, the raw materials are first treated with alkali. For this step, solutions of NaOH are used in concentrations from 0.2–4% by weight. The fats are saponified, and any accompanying proteins sensitive to alkalis are eliminated together with any other substances sensitive to alkalis, such as glycosaminoglycans, proteoglycans, etc. The process is controlled by determining the amide nitrogen. At the end of the alkaline treatment the level of amide nitrogen should be between 0.3 and 0.5 mmol/g.

The second step is the treatment of the material with inorganic acid, usually HCl. Acid-sensitive contaminants are eliminated, the fibres are greatly swollen and in this way the fibrous structure is loosened. Acidification is continued until the material is homogeneously acidified.

After this, the material is washed. It has proved useful to wash the material until the pH has changed from 0.5–1.5 (during acidification with HCl) to between 2.5–3.5. The washing is preferably carried out with distilled water.

The swollen material can now be levelled out (split), to achieve a uniform thickness. Further steps include a de-swelling operation, neutralisation and thorough washing of the material. For this, the material is first treated with an acidic (pH 2.8–3.5) common salt solution (concentration 5–10% by weight). The material is thus completely de-swollen. It is then washed with excess of slightly alkaline distilled water until the pH of the material reaches 5.8–6.5. The material is then thoroughly washed with distilled water (pH 6.0). This brings to an end the first phase of production, namely purification. This is followed by drying and degreasing.

The material is dried by repeated washing with acetone. This causes shrinkage of the collagen fibres and, as a result, an open structure remains. The degreasing is carried out with n-hexane. This eliminates the last traces of hydrophobic substances from the material.

The dry thickness of the membrane for use in guided tissue regeneration according to the present invention should ideally be between 0.1 and 1.0 mm but can be influenced by swelling of the material.

The membrane may thus be split or sectioned to achieve the required thickness, provided that the dual textures of the membrane are maintained.

The membrane may further be treated to adapt its properties to suit a particular wound type. Thus, the collagen of the membrane may be cross-linked to stabilise the membrane and reduce the rate of absorption by the body.

All the crosslinking agents known hitherto and used for medical products can be used for the membranes (e.g. formaldehyde, glutardialdehyde, hexamethylenediisocyanate, dicyclohexylcarbodiimide, etc.). Physically, crosslinking may be carried out by the application of heat. In this case the crosslinking effect is admittedly smaller but is sufficient for most applications. Conveniently the collagen of the membrane is physically crosslinked by heating to 100°–120° C. (for 30 minutes to 5 hours), thereby extending the degradation time.

Conveniently the degree of cross-linking introduced will be such that the rate of reabsorption of the membrane correlates with the growth of the new tissue and healing of the wound. For example, osteocytes take approximately 6 weeks to regenerate a tooth cavity and thus a membrane which is absorbed in a period of 8–12 weeks would be suitable for lining that wound type. Clearly the membrane should not be heavily cross-linked otherwise the rate of absorption would be too slow and in extreme cases the membrane becomes non-absorbable.

One other modification which may be made to the membrane is to coat or impregnate the fibrous side with a glycosaminoglycan (GAG) such as hyaluronic acid, chondroitin sulphate, dermatan sulphate or keratan sulphate.

Glycosaminoglycans such as hyaluronic acid are important as regulatory molecules which affect tissue structure. They have a favourable influence on:

cell infiltration the formation and degradation of the fibrin matrix swelling of the matrix phagocytosis
vascularisation Shortly after injury the content of GAG in a wound increases. Hyaluronic acid and related GAGs bind to fibrin and form a three dimensional matrix (clot) which is interwoven within the fibrin matrix. The original fibrin matrix is thereby deformed, swells and becomes more porous. This permits better and faster infiltration and migration of the cells into the matrix.

Hyaluronic acid and fibrinogen react specifically with one another, even if one or other molecule is in a solid state.

In the inflammatory stage of injury hyaluronic acid stimulates granulocyte function, alters the properties of the surface of polymorphonuclear leukocytes and regulates the phagocytosis activity of cells.

During the conversion and breakdown of the hyaluronic acid fibrin matrix, smaller fragments of hyaluronic acid are produced. Small fragments of hyaluronic acid stimulate the construction of new blood vessels.

Additionally, GAGs such a hyaluronic acid make collagen incapable of provoking an immune reaction in a host animal. In order to achieve this the collagen must be reacted with at least one weight percent of GAG acid.

GAGs are carrier for structural and biologically active proteins. It has been found that GAG protein complex plays a very important part in scar-free wound healing in the fetus.

For these reasons impregnation of the collagen membrane with GAGs such as hyaluronic acid causes improved tissue regeneration within a wound or bone lesion.

In a further aspect, the present invention provides a membrane for use in guided tissue regeneration, one side of said membrane having a smooth texture, the opposite side having a fibrous texture, said membrane being impregnated with one or more GAGs.

Preferably, the GAG concentration increases through the thickness of the membrane, with the highest concentration of GAG being on the fibrous side of the membrane.

The GAG material may be introduced into the membrane as a gel which is spread onto the fibrous side of the membrane and then allowed to dry. This approach achieves a decreasing concentration gradient down into the membrane whilst the GAG does not completely penetrate through the membrane.

Whilst we do not wish to be bound by theoretical considerations, it is believed that the chains of the high MW GAGs act to guide the new cells down onto the membrane surface which can then act as a support for cell growth.

It is thus particularly beneficial that the fibrous side of the membrane is in the form of a composite matrix including GAGs.

Hyaluronic acid and other GAGs naturally in the body with the skin containing 19% and the peritoneum 13% (by weight hyaluronic acid. As naturally occurring substances GAGs do not cause any problems regarding toxicity or resorption, but rather are believed to act as a natural nutritional substance for the cells. Hyaluronic acid and other GAGs are produced industrially and are thus readily available in commercial quantities.

Conveniently the membrane according to the present invention contains 0.1 to 30% by weight of a GAG, for example hyaluronic acid, for example 2–10% by weight.

If required other pharmaceuticals such as antibiotics (e.g. tetracycline), chemotherapeutics (e.g. taurolidine) and other drugs may also be incorporated into the membrane.

The present invention also provides the use of the resorbable membrane described above, optionally including one or more GAGs such as hyaluronic acid as additive in the manufacture of a component matrix for use as a guided tissue regeneration implant.

One particularly beneficial application of the membranes in guided tissue regeneration is after orafacial or dental surgery. Here it is often important for bone regeneration to take place, for example after partial removal of a tooth root or section of jaw. The constricted orofacial area makes surgery difficult and thus a non-toxic fully resorbable implant for guided tissue regeneration is highly advantageous. In addition, the nature of the membrane is particularly suited to encouraging the growth of osteocytes (bone tissue).

The present invention further provides a method of treating wounds or lesions of the human or non-human animal (preferably mammalian) body, said method comprising application of a membrane as described above to the wound or lesion, said membrane being orientated so that the fibrous side faces the area where tissue regeneration is required. The method is particularly suitable for the treatment of orofacial wounds or lesions.

Figure 1:
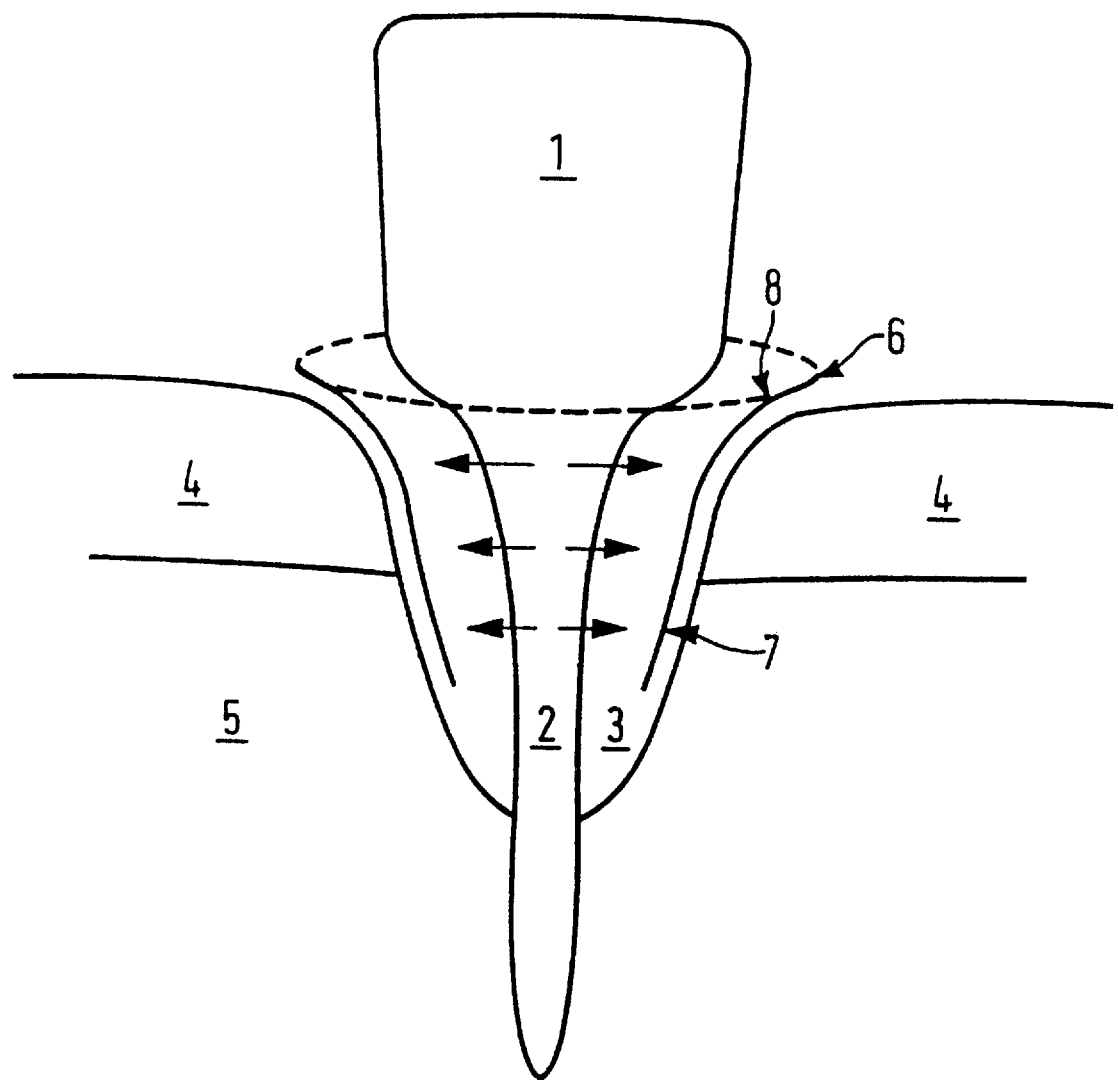
FIG. 1 shows a membrane according to the present invention in use for bone regeneration of a tooth (1) which has suffered heavy bone loss around the root (2) resulting in a cavity (3) normally filled by healthy root. The root (2) protrudes through a layer of connective tissue or gum (4) into a bone socket (5). To prevent ingrowth of connective tissue (4) into cavity (3) a membrane cover (6) is placed around the outermost edge of the wound. The membrane (6) extends all round the wound cavity (3). The membrane (3) has a smooth side (7) which faces away from cavity (3) and a fibrous side (8) which faces into cavity(3). The fibrous side (8) provides a supporting surface for new cells growing outward from root (2), whereas the smooth side (7) of the membrane (6) prevents cells of connective tissue (4) invading the wound cavity. Membrane (6) is resorbed slowly back into the body, optimally membrane absorption correlates to the time taken for wound healing.

The present invention may be further illustrated by means of the following non-limiting Example:

EXAMPLE

The peritoneal membranes from young calves are completely freed from flesh and grease by mechanical means, washed under running water and treated with 2% NaOH solution for 12 hours. The membranes are then washed under running water and acidified with 0.5% HCl. After the material has been acidified through its entire thickness (about 3 hours) the material is washed until a pH of 3.5 is obtained. The material is then shrunk with 7% saline solution, neutralised with 1% $NaHCO_3$ solution and washed under running water. The material is then dehydrated with acetone and degreased with N-hexane. The amide nitrogen content of the material is 0.47 mMole/g.

Determination of the Amide Nitrogen Content (Eastoe, E; Courts, A; Practical Analytical Methods for Connective Tissue Proteins (1963)).

Reagents

| | |
|---|---|
| 1. | 2 N HCl (160 ml of conc. HCl made up to 1 litre) |
| 2. | 0.05 M Borax - 0.15 N NaOH solution (19.1 g $Na_2B_4O_7 \cdot 10\ H_2O$) + 6 g NaOH in 1 litre, topped up with cold distilled $H_2O$. |

-continued

| 3. | Indicator - mixed in ethanol (0.33% methylene blue + 0.05% methylene red) |
| --- | --- |
| 4. | 1% boric acid with the indicator |
| | 10 g boric acid in 1 litre distilled cold $H_2O$ |
| | 8 ml indicator |
| | 0.7 ml 0.1 N - NaOH |
| 5. | 0.01 N HCl |

Method

| 1. | 1 g of dried collagen mass is dispersed in 50 ml of 2 N HCl and boiled for 1 hour. The volume is made up to 50 ml at 20° C. |
| --- | --- |
| 2. | 5 ml of this dispersion are placed in a microkjehldahl flask, together with 20 ml of solution 2; the micture is distilled in 20 ml of solution 4. Distillation takes 6 minutes. |
| 3. | The solution is titrated with reagent 5. |

Calculation ml of acid consumption × 20 = mmol % amide N

Example 1.36 ml of 0.01 N HCl × 20 = 27.2 mmol %
= 0.27 mmol/g amide N

We claim:

1. A resorbable collagen membrane for use in guided tissue regeneration comprising a substantially purified collagen membrane which is physiologically acceptable for implant into a mammalian body, and which is at least about 95% by weight native collagen, wherein a first face of said membrane is fibrous thereby allowing cell growth thereon and an opposite face of said membrane is smooth, thereby inhibiting cell adhesion thereon and acts as a barrier to prevent passage of cells therethrough.

2. A membrane as claimed in claim 1 which is derived from a natural collagen membrane.

3. A membrane as claimed in claim 2 derived from mammalian peritoneum or pericardeum, placenta membrane or basal membrane.

4. A membrane as claimed in claim 3 which is derived from calves or piglets.

5. A membrane as claimed in claim 4 which is derived from 6–7 week old piglets.

6. A membrane as claimed in claim 1 which is substantially free from fat.

7. A membrane as claimed in claim 1 which has a thickness of 0.1 to 1.0 mm when dry.

8. A membrane as claimed in claim 1 in which the collagen is cross-linked without becoming non-resorbable.

9. A membrane as claimed in claim 1 in which said first face is on a fibrous side of said membrane, and wherein the fibrous side is impregnated with a glycosaminoglycan.

10. A membrane as claimed in claim 9 in which the fibrous side is impregnated with hyaluronic acid.

11. A membrane as claimed in claim 9 in which the fibrous side is impregnated with a member selected from the group consisting of chondroitin sulphate, dermatan sulphate, keratan sulphate and mixtures thereof.

12. A membrane as claimed in claim 9 in which the membrane contains 0.1 to 30.0% by weight of glycosaminoglycan.

13. A membrane as claimed in claim 1 containing at least one pharmaceutical.

14. A membrane as claimed in claim 13 containing taurolidine.

15. A method of treating a wound or lesion of a human or non-human animal body comprising application of a membrane as claimed in claim 1 to the wound or lesion, said membrane being so oriented that the fibrous face of the membrane faces an area where tissue regeneration is required.

16. A method as claimed in claim 15 in which the said tissue is bone.

17. A method as claimed in claim 16 in which the wound or lesion is in an orofacial region.

18. A method of preparing a membrane as claimed in claim 1 in which a mammalian collagen membrane having a smooth face and a fibrous side having a fibrous face is subjected to treatment with alkali to saponify fats and eliminate alkali sensitive substances and then acidified to eliminate acid sensitive substances, followed by washing, drying, and degreasing, whereby to form a membrane comprising at least about 95% by weight native collagen.

19. A method as claimed in claim 18 in which, a glycosaminoglycan is impregnated into the fibrous side of said membrane.

20. A method of guided tissue regeneration comprising application of a resorbable collagen membrane to an orofacial region of a human or non-human animal body, wherein a first face of said membrane is fibrous thereby allowing cell growth thereon and an opposite face of said membrane is smooth, thereby inhibiting cell adhesion thereon and acts as a barrier to prevent passage of cells therethrough.

21. A method as claimed in claim 20 wherein said membrane comprises at least about 95% by weight native collagen.

22. A method as claimed in claim 20 in which the tissue is bone.

23. A method as claimed in claim 18 further including the step of cross-linking said membrane.

24. A membrane as claimed in claim 12, in which said membrane contains 2–10% by weight said glycosaminoglycan.

* * * * *